United States Patent [19]

Yoshida et al.

[11] Patent Number: 4,738,848

[45] Date of Patent: Apr. 19, 1988

[54] ANTI-INFLAMMATORY ANALGESIC ADHESIVE PREPARATION

[75] Inventors: Yuichi Yoshida, Toyama; Yoshihisa Nakano, Osaka; Tetsuo Horiuchi, Osaka; Toshinobu Tsuda, Osaka; Mitsuru Tamada, Osaka, all of Japan

[73] Assignees: Nitto Electric Industrial Co., Ltd.; Ikeda Mohando Co., Ltd., both of Japan

[21] Appl. No.: 870,464

[22] Filed: Jun. 4, 1986

[30] Foreign Application Priority Data

Jun. 4, 1985 [JP] Japan .................................. 60-122291

[51] Int. Cl.⁴ .............................................. A61L 15/00
[52] U.S. Cl. .................... 424/448; 424/449; 424/469
[58] Field of Search ........................ 424/469, 448, 449

[56] References Cited

U.S. PATENT DOCUMENTS 3,598,122  8/1971  Zaffaroni ........................... 424/449
3,598,123  8/1971  Zaffaroni ........................... 424/449
3,632,740  1/1972  Robinson et al. .................. 424/448

Primary Examiner—Thurman K. Page
Assistant Examiner—Leon R. Horne
Attorney, Agent, or Firm—Sughrue, Mion, Zinn, Macpeak & Seas

[57] ABSTRACT

An anti-inflammatory analgesic adhesive preparation is disclosed, comprising a flexible support having laminated thereon a pressure-sensitive adhesive material layer which contains Diclofenac Sodium and an organic acid such as citric acid. This adhesive preparation has excellent percutaneous absorption properties.

12 Claims, No Drawings

ANTI-INFLAMMATORY ANALGESIC ADHESIVE PREPARATION

FIELD OF THE INVENTION

The present invention relates to an anti-inflammatory analgesic adhesive preparation containing diclofenac sodium ([o-(2,6-dichloroanilino)phenyl]acetic acid sodium salt) having excellent percutaneous absorption properties.

BACKGROUND OF THE INVENTION

Diclofenac sodium which is a non-steroidal drug, has an excellent anti-inflammatory analgesic, antipyretic effect as in Indomethacin and the utility thereof is highly evaluated. Therefore, diclofenac sodium is widely used as a tablet or a suppository in a clinical field.

Declofenac sodium, however, has a disadvantage to cause various side effects such as gastro-intestinal lesion when orally administered. In order to minimize such side effects, attempts are made to administer diclofenac sodium in an enteric tablet or as a suppository. However, the use thereof is restricted for patients having the gastrointestinal lesion.

Recently, in order to overcome the above problems, various ointments and adhesive preparations containing diclofenac sodium as an effective component have been developed. They are expected to exhibit excellent local action and to prevent the side effects such as the gastrointestinal lesion by applying to an inflammatory site so as to percutaneously absorb the effective component.

However, the skin has a stratum corneum containing keratin as a main component and contains a large amount of a fat-soluble component such as fat, wax and cholesterol. Therefore, the skin has a physiological defensive function, a so-called "barrier function", and as a result, it is difficult to easily make a percutaneous absorption of the drug. Against drugs having a salt form, such as diclofenac sodium, the skin exhibits a strong barrier function.

The other side, the skin adhesive preparations are comprised of rubber or acrylic high molecular weight material as a base material. These materials generally do not dissolve drugs sufficiently, and it is quite difficult to uniformly dissolve the drug having the salt form such as diclofenac sodium and maintain the dissolved state. Even if the drug in the skin adhesive preparation is prepared in the dissolved state, crystallization of the drug contained occurs during storage, sometimes inhibiting the percutaneous absorption of the drug.

SUMMARY OF THE INVENTION

As a result of extensive investigations on an adhesive preparation which overcomes the above disadvantages, and increases the solubility and percutaneous absorption of diclofenac sodium, thereby effectively exhibiting the effect in treating disease, it has been found that if diclofenac sodium is contained in a pressure-sensitive adhesive material layer in combination with an organic acid, diclofenac sodium can be converted to free-based Diclofenac in the pressure-sensitive adhesive material layer. As a result, the solubility of diclofenac sodium is increased and the transfer of the drug to the skin surface is facilitated, whereby diclofenac sodium can easily penetrate through the stratum corneum as a barrier layer.

Accordingly, an object of the present invention is to provide an anti-inflammatory analgesic adhesive preparation comprising a flexible support having laminated thereon a pressure-sensitive adhesive material layer containing diclofenac sodium and an organic acid.

DETAILED DESCRIPTION OF THE INVENTION

The pressure-sensitive adhesive material layer which can be used in the present invention is a layer containing and maintaining diclofenac sodium as an effective component and an organic acid as an additive for increasing solubility and percutaneous absorption of diclofenac sodium. The material for such layer is not limited so long as it is a material capable of adhering to the skin surface.

Examples of acrylic pressure-sensitive adhesive materials selected from the standpoints of adhesive properties to the skin and stability of the drug are homo- or copolymers of at least one of alkyl esters of (meth)acrylic acid such as butyl (meth)acrylate, pentyl (meth)acrylate, hexyl (meth)acrylate, heptyl (meth)acrylate, octyl (meth)acrylate, nonyl (meth)acrylate, decyl (meth)acrylate, undecyl (meth)acrylate, dodecyl (meth)acrylate, and tridecyl (meth)acrylate, a copolymers of at least one of the above esters and other monomers copolymerizable therewith.

Examples of the copolymerizable monomer include carboxyl group-containing monomers such as (meth)acrylic acid, itaconic acid, crotonic acid, maleic acid, maleic anhydride and fumaric acid; sulfoxyl group-containing monomers such as styrenesulfonic acid, arylsulfonic acid, sulfopropyl acrylate, (meth)acryloyloxynaphthalenesulfonic acid, acrylamidomethylpropanesulfonic acid and acryloyloxybenzenesulfonic acid; hydroxyl group-containing monomers such as hydroxyethyl (meth)acrylate and hydroxypropyl (meth)acrylate; amide group-containing acrylic monomers such as (meth)acrylamide, dimethyl(meth)acrylamide, N-butylacrylamide, tetramethylbutylacrylamide and N-methylol(meth)acrylamide; alkylaminoalkyl group-containing acrylic monomers such as aminoethyl (meth)acrylate, dimethylaminoethyl (meth)acrylate, diethylaminoethyl (meth)acrylate and tert-butyl (meth)acrylate; alkyl esters of acrylic acid containing an ether bond in the molecule thereof such as methoxyethyl (meth)acrylate, ethoxyethyl (meth)acrylate, butoxyethyl (meth)acrylate, tetrahydrofurfuryl (meth)acrylate, methoxyethylene glycol (meth)acrylate, methoxydiethylene glycol (meth)acrylate, methoxypolyethylene glycol (meth)acrylate and methoxypolypropylene glycol (meth)acrylate; vinyl monomers such as N-(meth)acryloylamino acid; functional monomers such as acrylic monomers such as urethane, urea or isocyanate ester of acrylic acid; and vinyl monomers such as (meth)acrylonitrile, vinyl acetate, vinyl propionate, vinyl pyrrolidone, vinyl pyridine, vinyl pyrazine, vinyl piperadine, vinyl piperidone, vinyl pyrimidine, vinyl pyrrole, vinyl imidazole, vinyl caprolactam, vinyl oxazole, vinyl thiazole, vinyl morpholine, styrene, α-methylstyrene and bis(N,N'-dimethylaminoethyl) maleate.

The above alkyl esters of (meth)acrylic acid and copolymerizable monomers include isomers in which the alkyl portion is straight or branched, and isomers and derivatives in which the position of substituents is different.

As materials having low skin irritating properties and good solubility to drugs, pressure-sensitive adhesive materials comprising copolymers of an alkyl ester of (meth)acrylic acid, an alkyl ester of (meth)acrylic acid containing an ether bond in the molecule and copolymerizable monomers other than the above-described monomers are particularly used.

It is desirable from a standpoint of the balance between adhesive properties to the skin and cohesion that the ratio of the alkyl ester of (meth)acrylic acid to the copolymerizable monomer in the acrylic pressure-sensitive adhesive material is 50:50 to 99:1 by weight. When alkyl esters of (meth)acrylic acid containing an ether bond in the molecule thereof are used from the standpoint of the low skin irritating properties, it is desirable that the ratio of the alkyl ester of (meth)acrylic acid/the alkyl ester of (meth)acrylic acid containing an ether bond in the molecule/the other copolymerizable monomer is 40 to 80/59 to 10/1 to 40.

Other pressure-sensitive adhesive materials which can be used include rubbers such as silicone rubber, polyisoprene rubber, polyisobutylene rubber, polybutadiene, styrene-butadiene (or isoprene)-styrene block copolymer rubber, acrylic rubber and natural rubber; vinyl-based high molecular weight materials such as polyvinyl alkyl ether, polyvinyl acetate, a partially saponified product of polyvinyl acetate, polyvinyl alcohol and polyvinyl pyrrolidone; cellulose derivatives such as methyl cellulose, carboxymethyl cellulose and hydroxypropyl cellulose; polysaccharides such as pullulan, dextrin and agar; polyurethane elastomers; and polyester elastomers.

When the above composition is used, in the case where there is a trouble that after adhering to the skin, it causes the phenomenon of adhesive transfer on the applied skin, thereby contaminating the skin surface, it is preferred that the composition is subjected to suitable chemical crosslinking treatment (e.g., copolymerization of crosslinkable monomers and addition of a crosslinking agent) or physical crosslinking treatment (e.g., irradiation with ultraviolet rays and ionizing radiations such as electron beam) to such an extent of not deteriorating the adhesive properties to the skin.

The amount of diclofenac sodium used as effective component in the present invention is not limited so long as the therapeutic effect is exhibited. The amount of diclofenac sodium in the pressure-sensitive adhesive material is generally 1 to 40 wt% and preferably 5 to 30 wt% based on the weight of the pressure-sensitive adhesive material, and 20 to 1,600 $\mu g/cm^2$ and preferably 100 to 1,200 $\mu g/cm^2$ per unit area.

Since diclofenac sodium used in the present invention is in a salt form, it is difficult to dissolve a large amount of diclofenac sodium in the pressure-sensitive adhesive material layer which has relatively high lipophilic properties and maintain diclofenac sodium therein. Even if it is added in a large amount, in some cases all the drug cannot be dissolved or the crystallization of the drug occurs, making it impossible to diffuse a sufficient amount of the drug to the skin surface.

The present invention overcomes this problem by concurrently using an organic acid. The use of the organic acid increases the solubility of diclofenac sodium in the pressure-sensitive adhesive material layer and also the percutaneous absorption properties.

It is believed that the reason for this is that since by concurrently using diclofenac sodium and the organic acid, diclofenac sodium is converted into free-based Diclofenac having higher oleophilicity, the solubility of diclofenac sodium in the pressure-sensitive adhesive material layer is increased and diclofenac sodium can easily penetrate through the stratum corneum having the barrier function, viz., the percutaneous absorption properties are increased.

This characteristic is the greatest effect of the present invention, and a sufficient solubility cannot obtained even if free-based Diclofenac is contained alone or free-based Diclofenac and organic acid are concurrently present.

As such organic acids, it is preferred to use acids stronger than free-based Diclofenac and carboxylic acids are particularly preferred. Examples of carboxylic acids include citric acid, succinic acid, lactic acid, maleic acid, fumaric acid, salicylic acid and acetic acid. In particular, if citric acid is used, the solubility of diclofenac sodium in the pressure-sensitive adhesive material layer and the percutaneous absorption properties are markedly increased.

The amount of the organic acid added in the pressure-sensitive adhesive material layer is 5 to 100 parts by weight, preferably 10 to 40 parts by weight, per 100 parts by weight of diclofenac sodium.

In order to obtain the adhesive preparation which can be effectively used for the treatment of diseases, it is desired that at least 50%, preferably at least 80%, of diclofenac sodium is converted into and present in the form of free-based Diclofenac in the pressure-sensitive adhesive material layer.

As a support on which the pressure-sensitive adhesive material layer containing diclofenac sodium and an organic acid is provided, a material having a flexibility is chosen in order to conform to the movement of the skin surface. Examples of the supports are a plastic film, nonwoven fabrics, woven fabrics, paper, a metallic foil, a foamed film or combinations thereof.

As described above, in the anti-inflammatory analgesic adhesive preparation of the present invention, diclofenac sodium which is sparingly soluble is incorporated in a pressure-sensitive adhesive material in combination with an organic acid to thereby increase the solubility of diclofenac sodium and the percutaneous absorption properties. Thus, the anti-inflammatory analgesic adhesive preparation of the present invention is effective in the treatment of inflammation and painful diseases.

The present invention is described in greater detail by reference to the following examples. The present invention, however, is not to be construed as limited to the following examples. In the examples, all parts are by weight unless otherwise indicated.

EXAMPLE 1

55 Parts of 2-ethylhexyl acrylate, 30 parts of methoxyethyl acrylate, 15 parts of vinyl acetate and 0.3 part of azobisisobutyronitrile were placed in a four-necked flask and the mixture was heated to a temperature of 60° to 63° C. in an inert gas atmosphere to initiate the polymerization reaction. The reaction was continued for 10 hours while controlling the reaction temperature by adding dropwise 125 parts of ethyl acetate. The reaction solution was further aged for 2 hours at 75° to 80° C. to prepare a copolymer solution.

To the copolymer solution thus obtained were added diclofenac sodium and citric acid in such amounts that the contents of diclofenac sodium and citric acid after drying were 20 wt% and 4 wt% based on the weight of the pressure-sensitive adhesive material layer, respectively, and the resulting mixture was coated on a releasing liner made of a polyester in such an amount that the drug content was 400 μg/cm² and then dried to prepare a pressure-sensitive adhesive material layer.

This pressure-sensitive adhesive material layer is transferred to an nonwoven fabric with an ethylene-vinyl acetate copolymer film (vinyl acetate content: 28 wt%) having a thickness of 40 μm laminated thereon at the ethylene-vinyl acetate copolymer layer side to produce an anti-inflammatory analgesic adhesive preparation of the present invention.

EXAMPLE 2

95 Parts of 2-ethylhexyl acrylate, 5 parts of acrylic acid and 0.2 part of benzoyl peroxide were placed in a four-necked flask and the mixture was heated to a temperature of 62° to 65° C. in an inert gas atmosphere to initiate the polymerization reaction. The reaction was continued for 8 hours while controlling the reaction temperature by adding dropwise 125 parts of ethyl acetate. The reaction solution was further aged for 2 hours at 75° to 80° C. to prepare a copolymer solution.

To the copolymer solution thus obtained were added diclofenac sodium and succinic acid in such amounts that the contents of diclofenac sodium and succinic acid after drying were 20 wt% and 6 wt% based on the weight of the pressure-sensitive adhesive material layer, respectively. The resulting mixture was coated on a releasing liner made of a polyester in such an amount that the drug content was 800 μg/cm², and then dried to prepare a pressure-sensitive adhesive material layer.

This pressure-sensitive adhesive material layer was transferred to an ethylene-vinyl acetate copolymer film (vinyl acetate content: 28 wt%) having a thickness of 30 μm to produce an anti-inflammatory analgesic adhesive preparation of the present invention.

EXAMPLE 3

100 Parts of isoprene rubber (molecular weight: 840,000), 30 parts of polybutene (molecular weight: 1,260) and 80 parts of an alicyclic saturated hydrocarbon resin (molecular weight: about 700; melting point: 100° C.) were dissolved in toluene and mixed.

To the 20 wt% adhesive solution thus obtained were added diclofenac sodium and citric acid in such amounts that the contents of diclofenac sodium and citric acid after drying were 10 wt% and 2 wt% based on the pressure-sensitive adhesive material layer, respectively, and the resulting mixture was coated on an ethylene-vinyl acetate copolymer film (vinyl acetate content: 28 wt%) having a thickness of 30 μm in such an amount that the drug content was 400 μg/cm² to form a pressure-sensitive adhesive material layer, thereby preparing an anti-inflammatory analgesic adhesive preparation of the present invention.

COMPARATIVE EXAMPLES 1 TO 3

The anti-inflammatory analgesic adhesive preparation was prepared in the same method as in Examples 1 to 3 (which correspond Comparative Examples 1 to 3, respectively) except that citric acid or succinic acid as the organic acid was not used.

The anti-inflammatory analgesic adhesive preparation produced in the above Examples and Comparative Examples were applied to rats and the concentration of diclofenac sodium in plasma was measured. The result are shown in Table 1.

TABLE 1

| | Concentration in plasma* Mean ± S.E. | |
|---|---|---|
| | After 2 hours (ng/ml) | After 4 hours (ng/ml) |
| Example 1 | 704.7 ± 138.0 | 676.8 ± 191.0 |
| Example 2 | 665.3 ± 126.1 | 513.4 ± 143.2 |
| Example 3 | 413.6 ± 101.5 | 367.1 ± 73.6 |
| Comparative Example 1 | 286.6 ± 68.9 | 213.5 ± 50.1 |
| Comparative Example 2 | 193.4 ± 53.2 | 165.6 ± 41.9 |
| Comparative Example 3 | 101.5 ± 32.4 | 83.1 ± 27.7 |

*The concentration in plasma was measured by the following method.
The adhesive preparations obtained in Examples and Comparative Examples each were applied to an abdominal side portion of a SD rat (weight: about 250 g) in a size of 3 cm × 4.5 cm. The concentration in plasma after 2 and 4 hours were measured by the conventional method. The number of animals was that each group consisted of 6 rats.

The transfer percentage and transfer amount of diclofenac sodium when the adhesive preparation was applied to the skin of human being were measured and the results are shown in Table 2. The transfer percentage and transfer amount were measured as follows.

The adhesive preparation having the same size as in the measurement of the concentration in plasma was applied for 24 hours and then peeled off. The residual diclofenac sodium in the adhesive preparation was extracted with methanol, and the transfer percentage and transfer amount to the skin surface were calculated from the initial content. Each value in the table is an average value of five subjects.

TABLE 2

| | Transfer Percentage (%) | Transfer Amount (μg/cm) |
|---|---|---|
| Example 1 | 15.6 | 70.8 |
| Example 2 | 12.1 | 97.4 |
| Example 3 | 9.6 | 40.1 |
| Comparative | | |
| Example 1 | 2.6 | 10.4 |
| Example 2 | 1.7 | 13.9 |
| Example 3 | 0.9 | 4.1 |

It can be seen from the above results that the adhesive preparation of the present invention can provide higher concentration in plasma and drug transfer amount to the human skin as compared with the comparative adhesive preparations. Therefore, the adhesive preparation of the present invention is effective in the treatment of diseases.

TEST EXAMPLE 1

The pressure-sensitive adhesive material layers were prepared in the same method as in Example 1 except that the amounts of diclofenac sodium and citric acid added were changed as shown in Table 3 below. The contents of diclofenac sodium and free-based Diclofenac in the pressure-sensitive adhesive material layer were measured.

The results obtained are shown in Table 3 below.

TABLE 3

| | Amount Added (Parts*) | | Content (%) | |
|---|---|---|---|---|
| Test No. | Diclofenac Sodium | Citric Acid | Diclofenac Sodium | Free-based Diclofenac |
| 1 | 10 | 0 | 100 | 0 |
| 2 | 10 | 2 | 11 | 89 |
| 3 | 20 | 4 | 18 | 82 |
| 4 | 20 | 6 | 1 | 99 |
| 5 | 30 | 4 | 50 | 50 |
| 6 | 30 | 6 | 21 | 79 |

TABLE 3-continued

| Test No. | Amount Added (Parts*) | | Content (%) | |
|---|---|---|---|---|
| | Diclofenac Sodium | Citric Acid | Diclofenac Sodium | Free-based Diclofenac |
| 7 | 30 | 8 | 4 | 96 |

*Parts by weight per 100 parts by weight of the pressure-sensitive adhesive material Quantitative analysis of diclofenac sodium and Free-Based Diclofenac Declofenac sodium and free-based Diclofenac are extracted from the sample (pressure-sensitive adhesive material layer) with methanol. The extract is evaporated to dryness, the residue is extracted with water/benzene. Free-based Diclofenac is extracted in a benzene layer and diclofenac sodium is extracted in an aqueous layer. Those are determined by the conventional liquid chromatography.

It can be understood from the data shown in Table 3 above that at least 50% of diclofenac sodium is converted into free-based Diclofenac by using diclofenac sodium in combination with citric acid.

TEST EXAMPLE 2

The adhesive preparations were prepared in the same method as in Example 1 except that diclofenac sodium+citric acid; free-based Diclofenac alone; and free-based Diclofenac+citric acid were added to the pressure-sensitive adhesive material layer in the amounts as shown in Table 4 below.

The adhesive preparations thus prepared were stored at room temperature and 40° C. for 1 day and 1 week, and the solubility of those compounds were visually judged.

The results obtained are shown in Table 4 below.

In Table 4 below, the numerical values show the amount of the indicated compound, parts by weight per 100 parts by weight of the pressure-sensitive adhesive material. For example, 10+2 means 10 parts by weight of diclofenac sodium+2 parts of citric acid.

TABLE 4

| | Diclofenac Sodium + citric acid | | | Free-based Diclofenac | | | Free-based Diclofenac + citric acid |
|---|---|---|---|---|---|---|---|
| | 10 + 2 | 20 + 4 | 30 + 6 | 10 | 20 | 30 | 20 + 4 |
| Room Temperature | | | | | | | |
| 1 Day | O | O | O | O | Δ | Δ | Δ |
| 1 Week | O | O | O | Δ | X | X | X |
| 40° C. | | | | | | | |
| 1 Day | O | O | O | Δ | Δ | X | Δ |

TABLE 4-continued

| | Diclofenac Sodium + citric acid | | | Free-based Diclofenac | | | Free-based Diclofenac + citric acid |
|---|---|---|---|---|---|---|---|
| | 10 + 2 | 20 + 4 | 30 + 6 | 10 | 20 | 30 | 20 + 4 |
| 1 Week | O | O | Δ | X | X | X | X |

O Dissolved
Δ Partially crystallized
X Crystallized

It is apparent from the results shown in Table 4 above that a sufficient solubility can be obtained by the concurrent use of diclofenac sodium and citric acid.

While the invention has been described in detail and with reference to specific embodiments thereof, it will be apparent to one skilled in the art that various changes and modifications can be made therein without departing from the spirit and scope thereof.

What is claimed is:

1. An anti-inflammatory analgesic adhesive preparation comprising a flexible support having laminated thereon a pressure-sensitive adhesive material layer which contains diclofenac sodium and a pharmaceutically acceptable carboxylic acid, wherein the amount of the pharmaceutically acceptable carboxylic acid is at least 5 parts by weight per 100 parts by weight of diclofenac sodium.

2. The preparation as in claim 1, wherein the carboxylic acid is selected from the group consisting of citric acid, succinic acid, lactic acid, maleic acid, fumaric acid, salicylic acid and acetic acid.

3. The preparation as in claim 2, wherein the carboxylic acid is citric acid.

4. The preparation as in claim 1, wherein the amount of the organic acid is 10 to 40 parts by weight per 100 parts by weight of diclofenac sodium.

5. The preparation as in claim 1, wherein the amount of diclofenac sodium is 1 to 40% by weight based on the weight of the pressure-sensitive adhesive material.

6. The preparation as in claim 5, wherein the amount of diclofenac sodium is 5 to 30% by weight based on the weight of the pressure-sensitive adhesive material.

7. The preparation as in claim 1, wherein the amount of diclofenac sodium is 20 to 1,600 $\mu g/cm^2$.

8. The preparation as in claim 7, wherein the amount of diclofenac sodium is 100 to 1,200 $\mu g/cm^2$.

9. The preparation as in claim 1, wherein the pressure-sensitive adhesive material is an acrylic pressure-sensitive adhesive material.

10. The preparation as in claim 9, wherein the acrylic pressure-sensitive adhesive material is a copolymer of an alkyl ester of (meth)acrylic acid, an alkyl ester of (meth)acrylic acid containing an ether bond in the molecule, and other copolymerizable monomer.

11. The preparation as in claim 10, wherein the acrylic pressure-sensitive adhesive material is a copolymer of 2-ethylhexyl acrylate, 2-methoxyethyl acrylate and vinyl acetate.

12. The preparation as in claim 10, wherein the proportion of the alkyl ester of (meth)acrylic acid/the alkyl ester of (meth)acrylic acid containing an ether bond in the molecule/the other copolymerizable monomer is 40 to 80/95 to 10/1 to 40.

* * * * *